(12) United States Patent
Booch et al.

(10) Patent No.: US 8,763,807 B2
(45) Date of Patent: Jul. 1, 2014

(54) PACKAGE FOR ABSORBENT ARTICLES

(75) Inventors: Thorsten Booch, Euskirchen (DE); Andreas Peter Motsch, Schwalbach am Taunus (DE); Fernando Bayod, Strombeek-Bever (BE)

(73) Assignee: The Procter & Gamble Company, Cincinnati, OH (US)

( * ) Notice: Subject to any disclaimer, the term of this patent is extended or adjusted under 35 U.S.C. 154(b) by 43 days.

(21) Appl. No.: 13/537,657

(22) Filed: Jun. 29, 2012

(65) Prior Publication Data
US 2013/0001124 A1  Jan. 3, 2013

(30) Foreign Application Priority Data
Jun. 30, 2011   (EP) ..................................... 11005375

(51) Int. Cl.
| B65D 73/00 | (2006.01) |
| B65D 85/00 | (2006.01) |
| B65D 6/28  | (2006.01) |
| B65D 5/32  | (2006.01) |

(52) U.S. Cl.
USPC .......... 206/494; 206/440; 206/526; 220/4.21; 229/87.01; 229/109

(58) Field of Classification Search
USPC ................ 206/438, 440, 494, 526, 581; 229/87.01–87.14, 108–110; 220/4.21, 220/4.24
See application file for complete search history.

(56) References Cited

U.S. PATENT DOCUMENTS

| 3,970,215 A | * | 7/1976 | McLaren et al. ............. 206/494 |
| 5,147,271 A |   | 9/1992 | Bacques et al. |
| 5,259,550 A |   | 11/1993 | Kuchenbecker |
| 5,934,470 A |   | 8/1999 | Bauer et al. |
| 6,705,465 B2 | * | 3/2004 | Ling et al. ..................... 206/440 |
| 7,179,246 B2 | * | 2/2007 | Hansson ....................... 206/440 |
| 7,328,833 B1 | * | 2/2008 | Wiley ......................... 229/108.1 |
| 7,455,214 B2 | * | 11/2008 | Miller et al. ................. 220/4.24 |
| 7,500,558 B2 | * | 3/2009 | Tanbo ......................... 229/87.12 |
| 7,938,263 B2 | * | 5/2011 | Vijay ......................... 229/87.01 |
| 8,261,914 B2 | * | 9/2012 | Hooyman et al. ............ 206/494 |
| 2010/0163609 A1 |   | 7/2010 | Bull |

FOREIGN PATENT DOCUMENTS

| EP | 0 468 860 A1 | 1/1992 |
| EP | 0 942 881 A1 | 9/1999 |
| WO | 98-24711 A1 | 6/1998 |

OTHER PUBLICATIONS

EP International Search Report, dated Oct. 14, 2011 (5 pages).
PCT International Search Report, mailed Nov. 29, 2012 (13 pages).

* cited by examiner

Primary Examiner — Bryon Gehman
(74) Attorney, Agent, or Firm — William E. Gallagher; Richard L. Alexander

(57) ABSTRACT

A package configuration for absorbent articles, such as disposable diapers, training pants and adult incontinence undergarments is disclosed. The package configuration may include one or more pluralities of absorbent articles, each plurality packaged in a flexible package. The one or more flexible packages may be wrapped and further contained by a wrap-around. The wrap-around may have first and second pairs of opposing side panels. Adjacent side panels from the first and second pair may be joined by corner panels. The corner panels may form interior angles with the side panels of from 100° to 170°. The presence of the angled corner panels may render the wrap-around better able to conform to the shape of the one or more flexible packages, and more resistant to deformation.

14 Claims, 12 Drawing Sheets

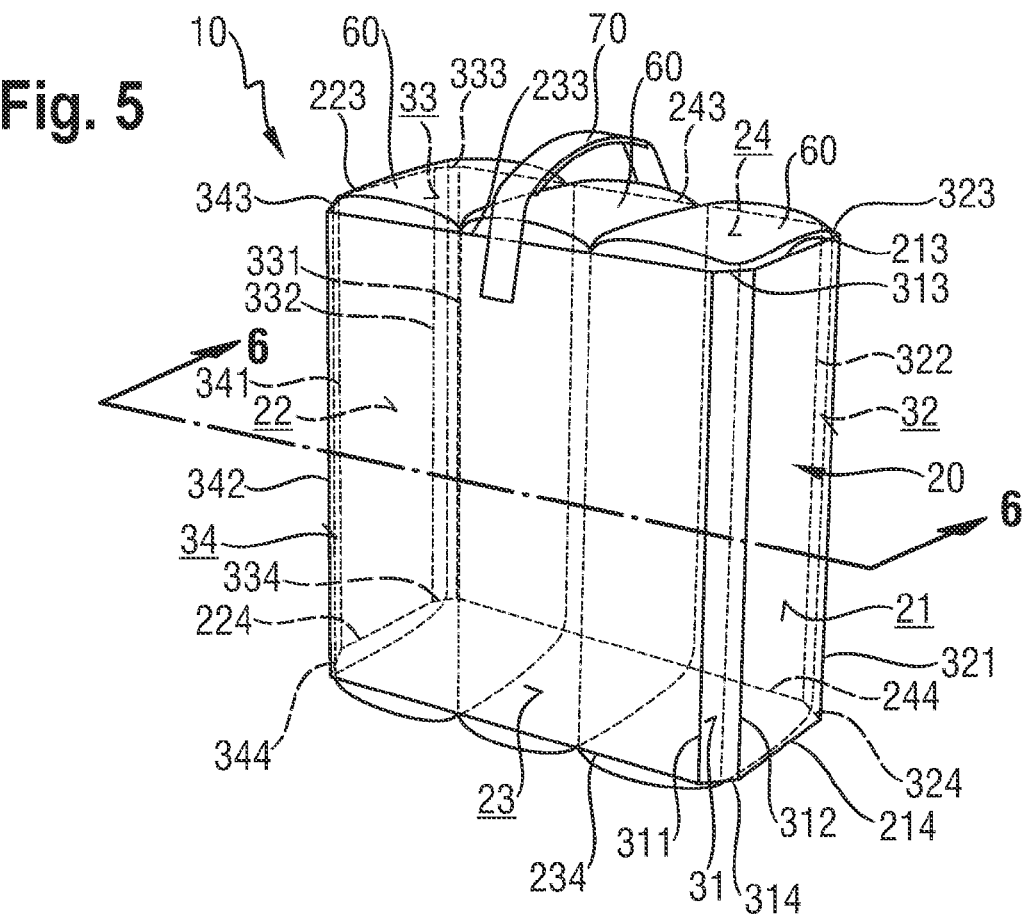

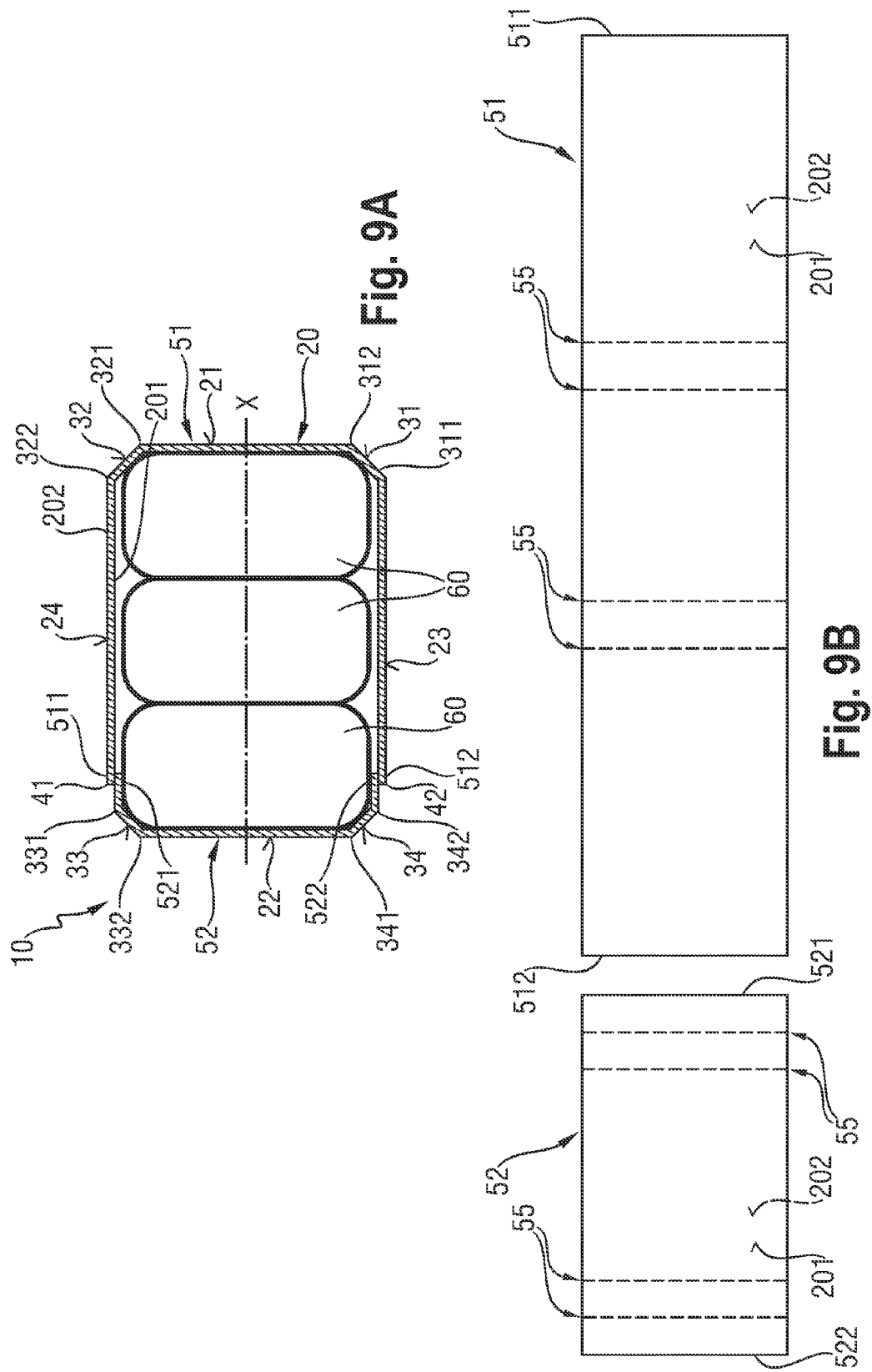

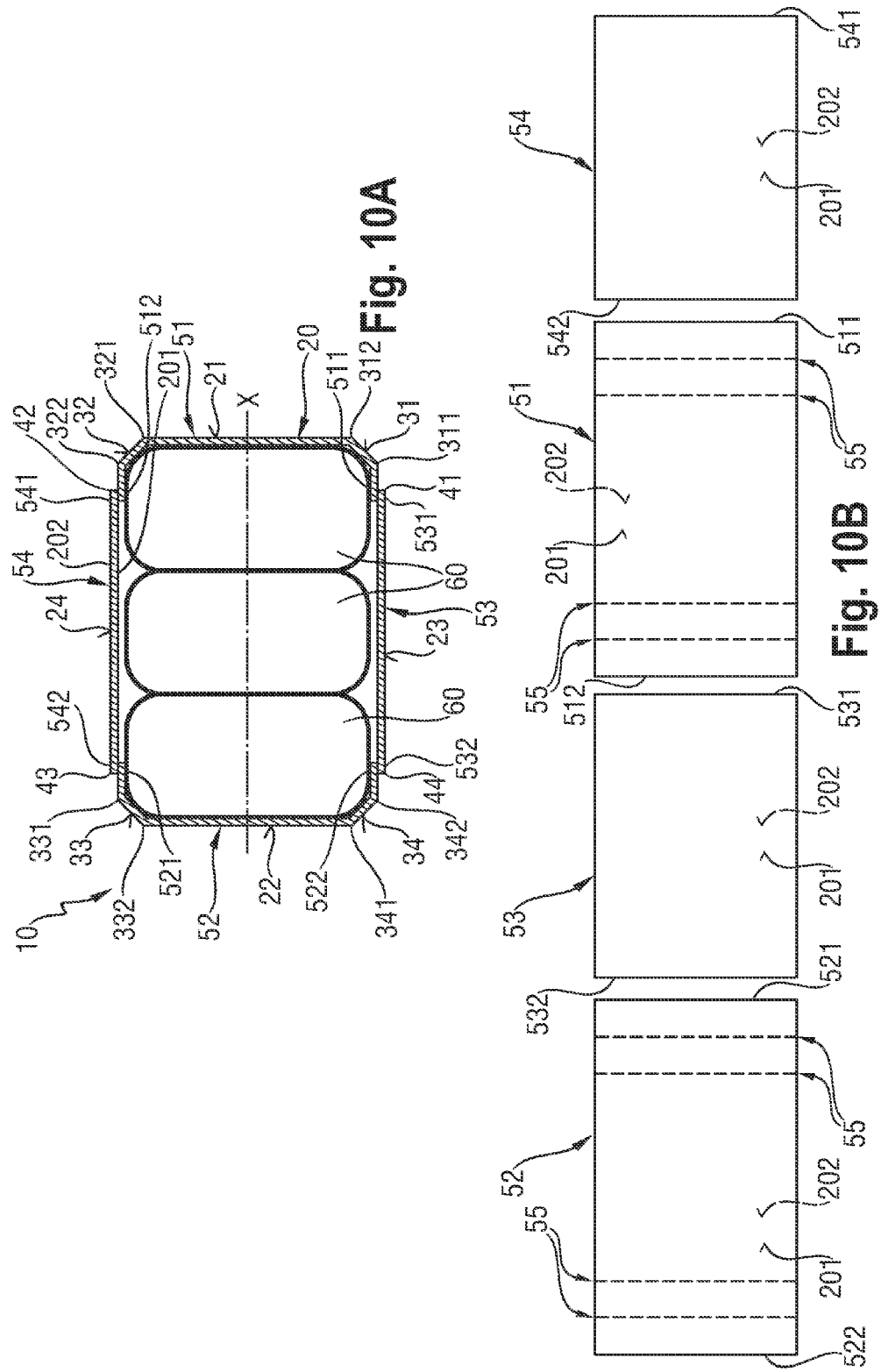

PACKAGE FOR ABSORBENT ARTICLES

CROSS REFERENCE TO RELATED APPLICATION

This application claims priority to European Patent Application No. EP 11005375.8, filed Jun. 30, 2011.

FIELD OF THE INVENTION

The present invention is directed to packages for absorbent articles, such as disposable diapers, training pants and adult incontinence undergarments.

BACKGROUND OF THE INVENTION

Absorbent articles such as diapers are typically packed in flexible packages such as packages made of films. However, only a limited amount of absorbent articles can be comprised in each package as otherwise the stability of the package may be adversely affected.

Non-flexible packages such as boxes made of cardboard or corrugated cardboard have been developed in order to contain more absorbent articles per package. Such packages typically comprise two or more individual flexible packages of densely packed absorbent articles. These packages typically have a parallelepiped shape. However, the problem with this type of packages is that the articles which are densely packed inside the package exert a force on the side panels of the package which may result in outward bending and buckling of the package.

Furthermore, such packages are typically stacked during storage. When a package is stacked upon another package, the upper package exerts a force on the lower package. This force may lead to additional deformation of the tower package.

The different deformations endured by a package may reduce the attractiveness of the package for the consumer. This may even convey the impression that the articles inside the package are of poor quality or have been damaged upon deformation of the package.

Therefore, there is a need for a package containing absorbent articles which is more resistant to deformation and still produced in a cost-effective manner.

BRIEF DESCRIPTION OF THE DRAWINGS

FIG. 5 is a perspective view of a package according to an embodiment of the present invention.

FIG. 6 is a cross-sectional view of the package of FIG. 5 taken at the section line 6-6.

FIG. 9A is a cross-sectional view of the package of FIG. 5 taken at the section line 6-6 comprising a wrap-around made of two pieces of material according to an embodiment of the present invention.

FIG. 9B is a plan view of the wrap around material comprised by the package of FIG. 9A.

FIG. 10A is a cross-sectional view of the package of FIG. 5 taken at the section line 6-6 comprising a wrap-around made of four pieces of material according to an embodiment of the present invention.

FIG. 10B is a plan view of the wrap around material comprised by the package of FIG. 10A.

DETAILED DESCRIPTION OF THE INVENTION

Figure 1:
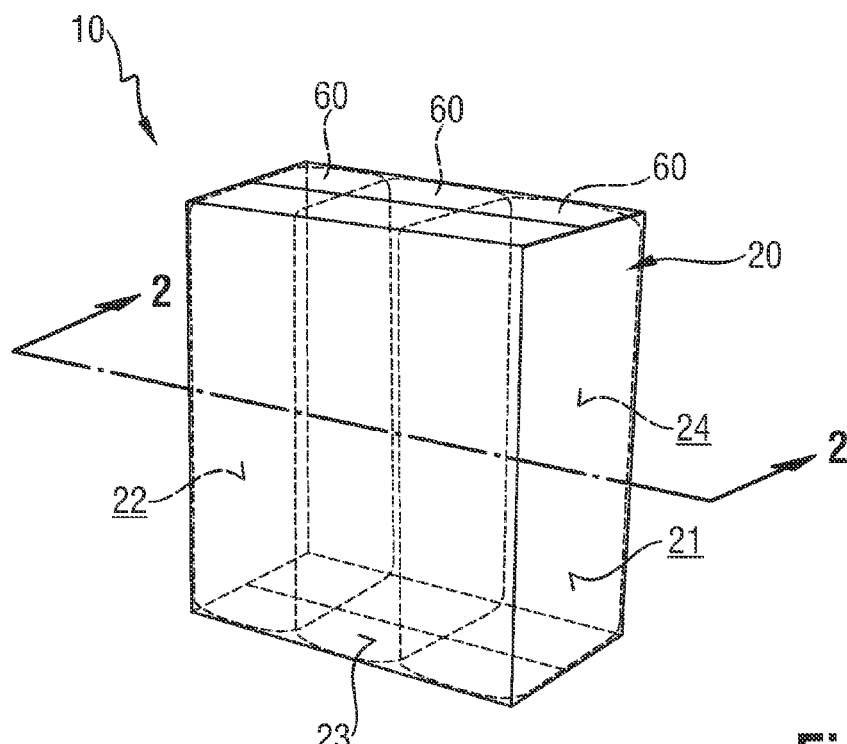
FIG. 1 is a perspective view of a package of the prior art
Figure 2:
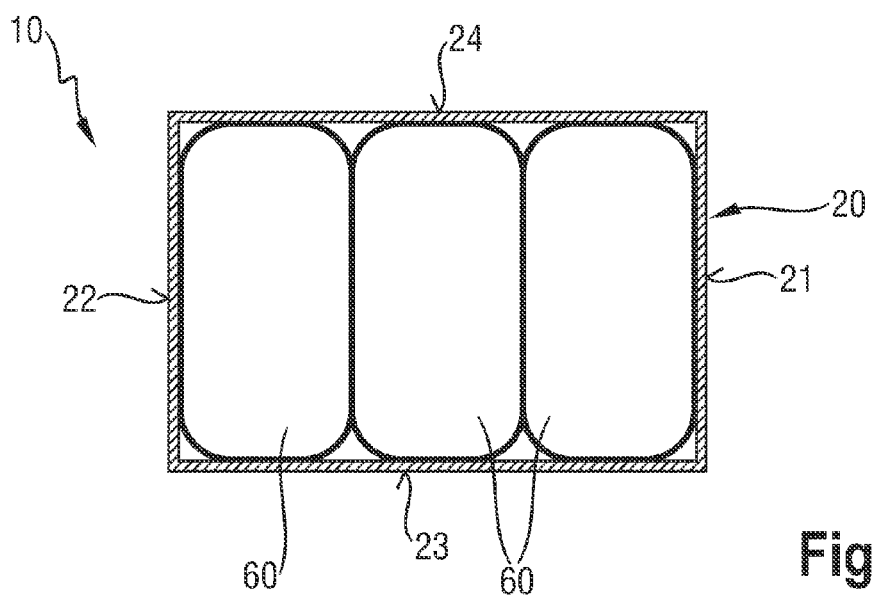
FIG. 2 is a cross-sectional view of the package of FIG. 1 taken at the section line 2-2.
Figure 3A:
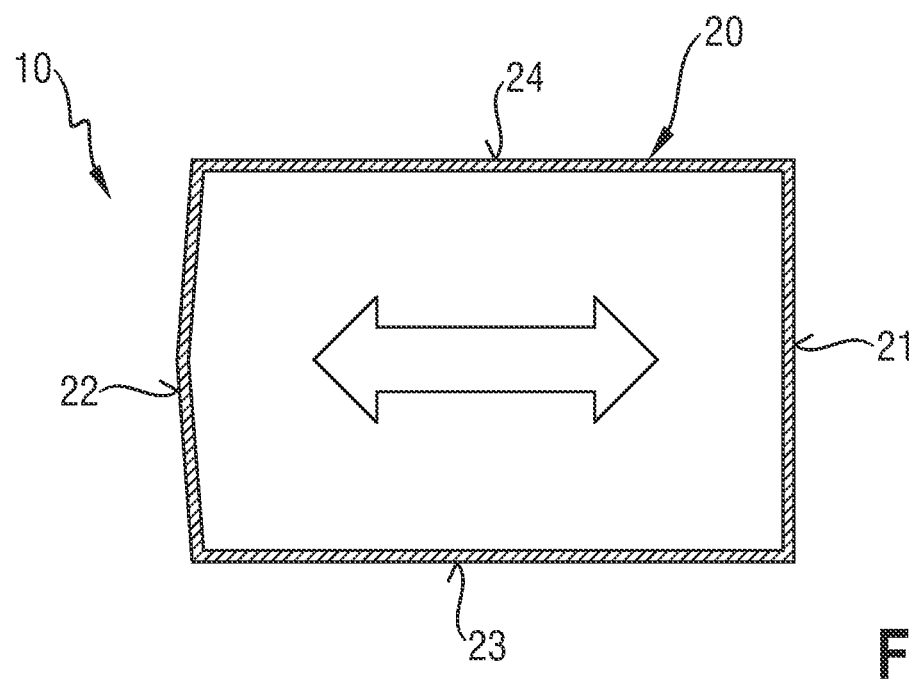
FIG. 3A is a schematic version of the cross-sectional view of the package of FIG. 1 taken at the section line 2-2 illustrating the force which is exerted by the flexible packages of absorbent articles which are comprised in the package on one of the side panels.
Figure 3B:
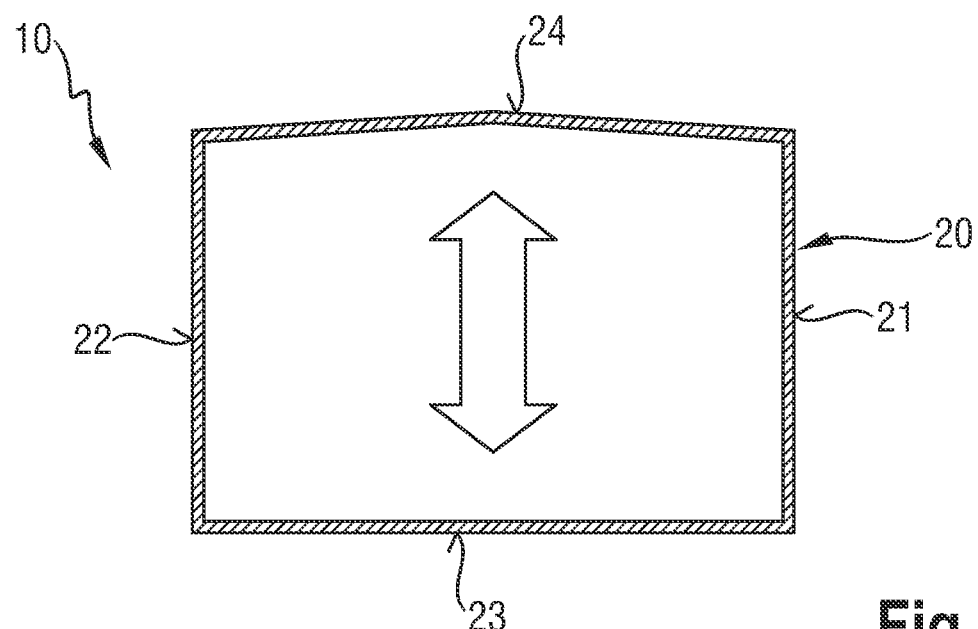
FIG. 3B is a schematic version of the cross-sectional view of the package of FIG. 1 taken at the section line 2-2 illustrating the force which is exerted by the flexible packages of absorbent articles which are comprised in the package on another side panel.
Figure 4:
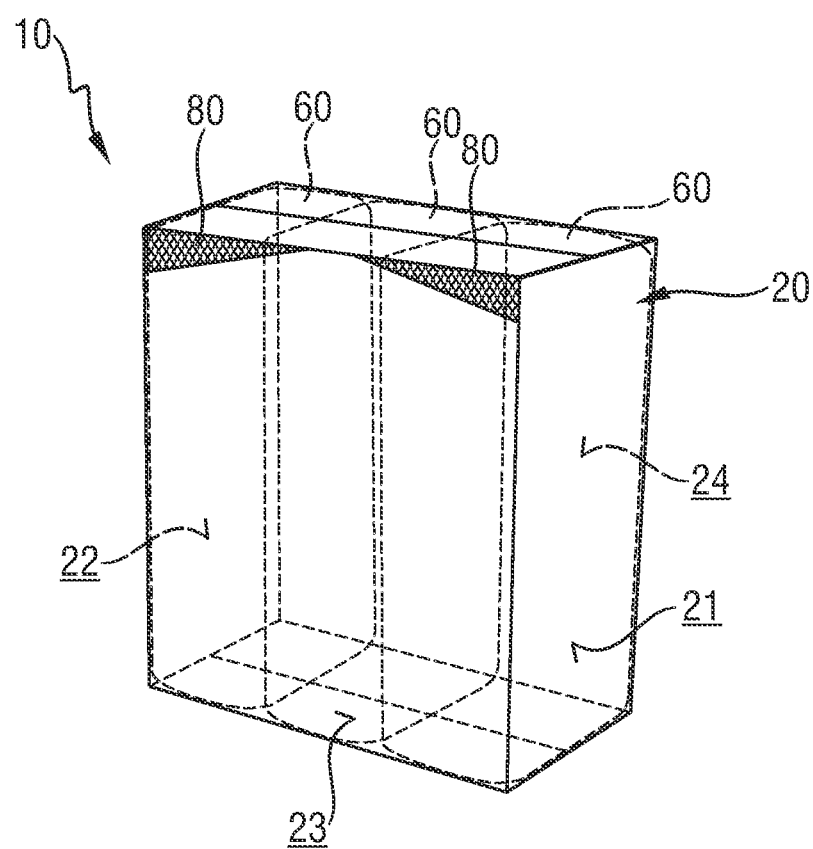
FIG. 4 is a perspective view of a package of the prior art representing the side portions of the edges of the package which endure a deformation when such packages are stacked during storage.

"Absorbent article" is used herein to refer to devices that absorb and contain body exudates, and, more specifically, refers to devices that are placed against or in proximity to the body of the wearer to absorb and contain the various exudates discharged from the body. Absorbent articles include diapers, training pants, adult incontinence undergarments, feminine hygiene products and the like. As used herein, the term "body fluids" or "body exudates" includes, but is not limited to, urine, blood, vaginal discharges, breast milk, sweat and fecal matter. In some embodiments of the present invention, the absorbent article is a diaper or training pant.

"Connect or connected" is used herein to refer to configurations whereby a first element is directly secured to another element by affixing the first element directly to a second element or whereby a first element is indirectly secured to a second element by affixing the first element to a third, intermediate member, which in turn is affixed to the second element. The term "connected" also encompasses configurations wherein the first and second elements are integral and, when a third element is present, configurations wherein the first, second and third elements are integral. As used herein, the term "integral" also encompasses embodiments wherein the first; second and/or third elements, are made of coextensive layers of material, for example coextensive layers of a corrugated cardboard material.

"Attached" is used herein to refer to configurations whereby a first element is directly secured to another element by affixing the first element directly to a second element "Connecting edge" is used herein to refer to one of the edges of a panel which is shared between two contiguous panels.

"Free edge" is used herein to refer to one of the edge of a panel which is not shared between two panels.

"Interior surface" is used herein to refer to the surface of a wrap-around or a side panel or a corner panel which is facing towards the flexible packages of absorbent articles which are wrapped by the wrap-around material.

"Exterior surface" is used herein to refer to the surface of the wrap-around or a side panel or a corner panel which is opposite to the interior surface of the wrap-around and facing away from the flexible packages of absorbent articles which are wrapped by the wrap-around material.

"Interior angle" is used herein to refer to the angle between the two interior surfaces of two contiguous panels of the package which is oriented toward the interior of the package.

The package 10 according to the present invention comprises one or more flexible packages of absorbent articles 60 which are wrapped by a wrap-around 20. The wrap-around 20 has an interior 201 and an exterior surface 202.

As for example shown in FIGS. 5 to 14, the wrap-around 20 comprises a first and a second opposing side panel 21, 22 which are parallel to each other and a third and a fourth side panel 23, 24 which are parallel to each other.

The wrap-around 20 further comprises at least a first corner panel 31 which connects one of the first and second side panels 21, 22 to one of the third and fourth side panel 23, 24. As for example shown in FIGS. 5 and 6, the first corner panel 31 connects the first side panel 21 to the third panel 23.

The interior angle α between the first corner panel 31 and the one of the first and second side panels 21, 22 is from 100° to 170° or 120° to 150° or 130° to 140° and the interior angle α between the first corner panel 31 and the one of the third and fourth side panels 23, 24 is from 100 to 170° or 120° to 150° or 130° to 140° as for example shown in FIG. 6.

As for example shown in FIGS. 1 to 4, a package 10 according to the prior art is typically a box of parallelepiped shape comprising flexible packages of absorbent articles 60. Such a box comprises four side panels 21, 22, 23, 24.

Since the flexible packages of absorbent articles 60 comprised in the package 10 are typically densely packed or compressed, they exert a force perpendicular to one or more of the side panels 21, 22, 23, 24. As for example shown in FIGS. 3A and 3B, the force exerted by the flexible package of absorbent articles 60 on one of the side panels 21, 22, 23, 24 may lead to outward bending of the package 10 and therefore deformation of the package 10.

Figure 7A:
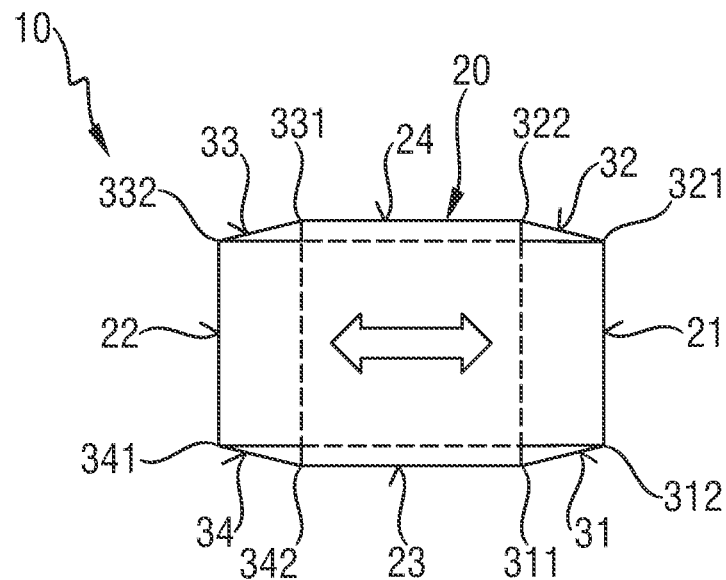
FIG. 7A is a schematic version of the cross-sectional view of the package of FIG. 5 taken at the section line 6-6 illustrating the force which is endured by one of the side panels due the flexible package of absorbent articles which are comprised in the package.
Figure 7B:
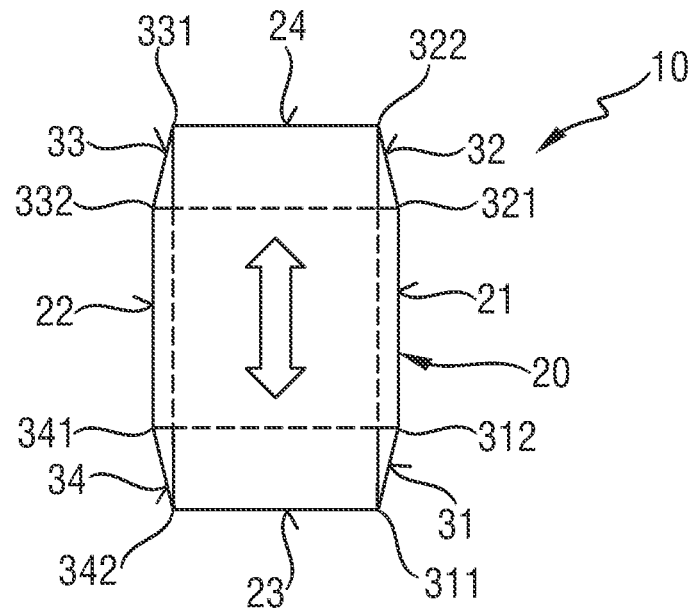
FIG. 7B is a schematic version of the cross-sectional view of the package of FIG. 5 taken at the section line 6-6 illustrating the force which is endured by another side panel due to the flexible packages of absorbent articles which are comprised in the package.

Hence, it is particularly advantageous to connect two side panels with a corner panel in order to reduce the risk of bending of the side panels to which the corner panel is connected. As can be seen in FIGS. 7A and 7B, the risk of bending of the side panels of a package 10 according to the present invention is reduced since the presence of the corner panel(s) 31, 32, 33, 34 allows for more flexibility of the package 10. Indeed, the corner panel(s) will help the wrap-around 20 to conform to the shape of the flexible packages 60.

In some embodiments, as for example shown in FIGS. 5 to 14, the wrap-around 20 further comprises a second, a third and a fourth corner panel 32, 33, 34 in addition to the first corner panel 31. In such embodiments, the first corner panel 31 connects the first and the third side panels 21, 23, the second corner panel 32 connects the first and the fourth side panels 21, 24, the third corner panel 33 connects the second and the fourth side panels 22, 24 and the fourth corner panel 34 connects the second and the third side panels 22, 23. In these embodiments, the interior angle α between each of the first, second, third and fourth corner panels 31, 32, 33, 34 and each of the two side panels to which the respective corner panel 31, 32, 33, 34 is connected is from 100° to 170° or 120° to 150° or 130° to 140°.

Shape of the Different Side Panels

As for example shown in FIG. 5, each of the first, second, third and fourth side panels 21, 22, 23, 24 comprises a pair of free opposing edges 213, 214, 223, 224, 233, 234, 243, 244 and a pair of connecting edges 312, 321, 322, 331, 332, 341, 342, 311. The connecting edges 312, 321, 322, 331, 332, 341, 342, 311 are typically parallel to each other.

The wrap-around 20 may comprise a first, second, third and fourth corner panels, as for example shown in FIG. 5, each of the first, second, third and fourth side panels comprises a pair of free opposing edges 313, 314, 323, 324, 333, 334, 343, 344 and a pair of connecting edges 312, 321, 322, 331, 332, 341, 342, 311.

The side panels 21, 22, 23, 24 and the corner panels 31, 32, 33, 34 may be rectangular shaped as for example shown in FIG. 5. These embodiments are advantageous since rectangular shaped panels are particularly easy to obtain from the raw material of which the wrap-around 20 is made with little to no waste material.

As can be seen in FIGS. 7A and 7B, the risk of bending of the side panels of a package 10 according to the present invention is reduced since the presence of the corner panel(s) 31, 32, 33, 34 allows for more flexibility of the package. Indeed, the corner panel(s) will help the wrap-around 20 to conform to the shape of the flexible packages of absorbent articles 60.

Figure 17:
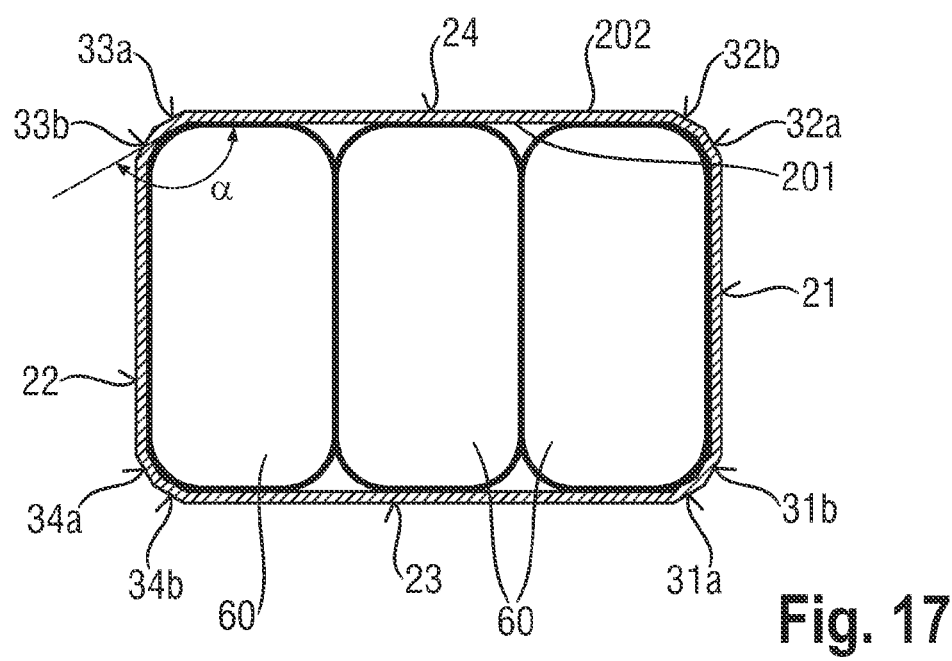
FIG. 17 is a cross-sectional view of the package of FIG. 5 taken at the section line 6-6, wherein each of the corner panels comprised by the wrap-around is divided into 2 sub-panels.

In some embodiments as for example shown in FIG. 17, at least one of the corner panels 31, 32, 33, 34 comprised by the wrap-around 20 is divided into 2 or more sub-panels 31a, 31b, 32a, 32b, 33a, 33b, 34a, 34b or 2 to 6 sub-panels having each a different orientation. Each of the first, second, third and fourth corner panels is divided into 2 or more sub-panels 31a, 31b, 32a, 32b, 33a, 33b, 34a, 34b or 2 to 6 sub-panels having each a different orientation as for example shown in FIG. 17. The first, second, third and fourth corner panels 31, 32, 33, 34 may be divided into two sub-panels or 3 or 4 sub-panels having each a different orientation.

It should be understood for the purpose of the invention that in the embodiments, wherein at least one of the corner panels 31, 32, 33, 34 comprised by the wrap-around 20 is divided into 2 or more sub-panels or 2 to 6 sub-panels having each a different orientation, the sub-panels have a flat width of 2 mm or more or 2 mm to 50 mm or 2 mm to 30 mm and the interior angle α between the at least one of the corner panels 31, 32, 33, 34 and one of the two side panels to which the corner panel is connected corresponds to the angle between the sub-panel of the corner panel 31, 32, 33, 34 which is contiguous to the side panel of the wrap-around as for example shown in FIG. 17.

Preferably, the first, second, third and fourth side panels 21, 22, 23, 24 have no sub-panels with different orientation.

Such a configuration of the package 10 may provide even more flexibility to the package 10 in order to help to conform to the shape of the flexible package(s) of absorbent articles 60.

The Wrap-Around

As mentioned above, the wrap-around 20 comprises an interior 201 and an exterior surface 202. The exterior surface 202 of the wrap-around 20 typically includes printed graphics such as artworks, trademarks, logos and/or regulatory information.

The wrap-around 20 may comprise or consist of cardboard material, corrugated board material and/or polymeric material.

In some embodiments, the wrap-around 20 comprises a hole or a window made of a transparent polymeric material which may be helpful in order to be able to see the flexible packages 60 from the outside of the wrap-around 20.

The wrap-around 20 may be made of a single piece of material or of two or more pieces of material which are attached to each other.

As used herein the term "attachment zone" refers to the overlap between the two opposing edges of a single piece of material which are attached to each other in order to form the wrap-around 20 in the embodiment wherein the wrap-around 20 is made of a single piece of material. The term "attachment zone" refers to the overlap between the edges of two different pieces of material which are attached to each other in order to form a portion of the wrap-around 20 in the embodiments wherein the wrap-around is made of two or more pieces of material.

The wrap-around 20 may be made of a single piece of material or of two or more pieces of material.

Embodiments Wherein the Wrap-Around is Made of One Piece of Material

Figure 8A:
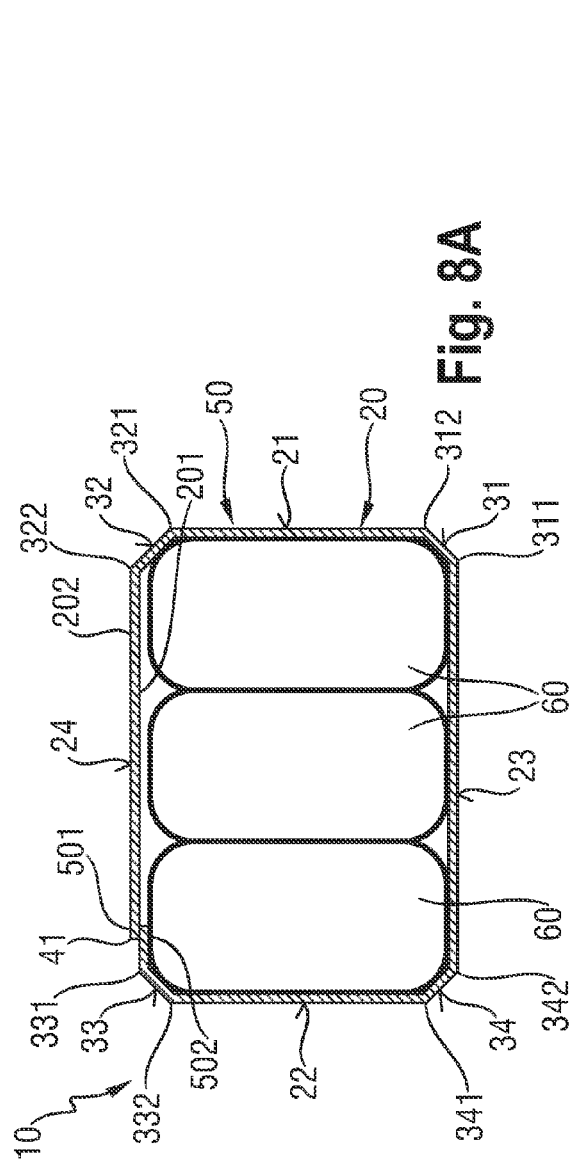
FIG. 8A is a cross-sectional view of the package of FIG. 5 taken at the section line 6-6 comprising a wrap-around made of a single piece of material according to an embodiment of the present invention.
Figure 8B:
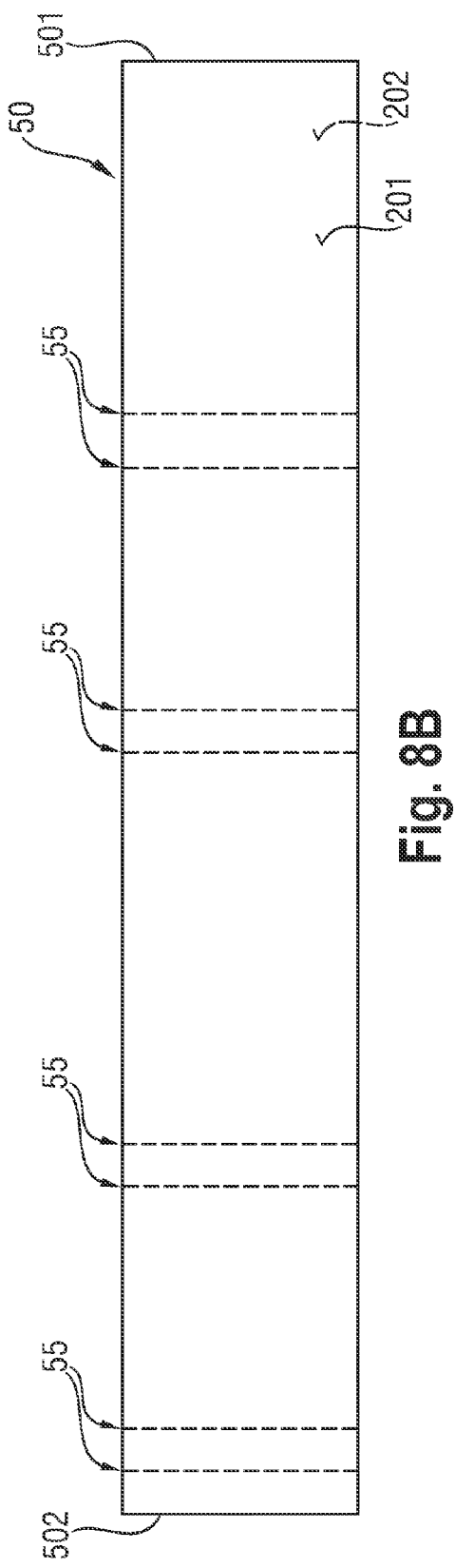
FIG. 8B is a plan view of the wrap around material comprised by the package of FIG. 8A.

The wrap-around 20 may be made of a single piece of material 50, as for example shown in FIGS. 8A and 8B. In such embodiments, the different panels of the wrap-around 20 are made by folding the single piece of material 50 along folding lines 55 which correspond to the connecting edges of the different panels of the wrap-around 20. Such folding lines 55 are typically parallel to each other.

As for example shown in FIGS. 8A and 8B, the single piece of material 50 may comprise a pair of opposing edges 501, 502 wherein the opposing edges 501, 502 of the single piece of material 50 are attached to each other along an attachment zone 41 in order to form the wrap-around 20 as for example shown in FIG. 8A.

The attachment zone 41 between the two opposing edges 501, 502 of the single piece of material 50 can take any position on the wrap-around 20.

As for example shown in FIG. 8A, the attachment zone 41 between the two opposing edges 501, 502 of the single piece of material 50 of which the wrap-around 20 is made may be positioned in close proximity to one of the corner panels 31, 32, 33, 34 of the wrap-around 20, i.e. from 1 mm to 100 mm, or 1 mm to 50 mm away from the corner panel. Such embodiments are particularly advantageous since the impact on the visual appearance of the package 10 is reduced. Indeed, the visual appearance of the package 10 is more affected if the attachment zone 41 is positioned close to the middle of one of the side panels and if therefore a graphic which is printed on the exterior surface of such side panels is interrupted by such an attachment zone 41 since. Indeed, in such a case good alignment of the two opposing edges 501, 502 is required.

Embodiments Wherein the Wrap-Around is Made of Two Pieces of Material

The wrap-around 20 may be made of two pieces of material 51, 52 as for example shown in FIGS. 9A and 9B. In such embodiments, a first piece of material 51 comprises the first side panel 21, a portion of the third and of the fourth side panels 23, 24 and both first and second corner panels 31, 32 and a second piece of material 52 comprises the second side panel 22, a portion of the third and of the fourth side panels 23, 24 and both third and fourth corner panels 33, 34.

The different panels of the wrap-around 20 may be made by folding each of the first and second pieces of material 51, 52 along folding lines 55 which correspond to the connecting edges 312, 321, 322, 331, 332, 341, 342, 311 of the different panels of the wrap-around 20. Such folding lines 55 are typically parallel to each other.

As for example shown in FIG. 9B, both the first and the second pieces of material 51, 52 may comprise a pair of opposing edges 511, 512, 521, 522 wherein one of the edges 511, 512 of the first piece of material 51 is attached to one of the edges 521, 522 of the second piece of material 52 along a first attachment zone 41 and wherein the other edge 511, 512 of the first piece of material 51 is attached to the other edge 521, 522 of the second piece of material 52 along a second attachment zone 42 in order to form the wrap-around 20.

The first and the second attachment zones 41, 42 can have any positioning on the wrap-around 20 but embodiments wherein each of the first and the second attachment zones 41, 42 are positioned in close proximity to one of the corner panels 31, 32, 33, 34 of the wrap-around 20, i.e. from 1 mm to 100 mm, or 1 mm to 50 mm away from the corner panel are particularly advantageous for the same reasons as mentioned above for the embodiments wherein the wrap-around 20 is made of a single piece of material.

The embodiments wherein the wrap-around 20 is made of two pieces of material 51, 52 are particularly advantageous since the first and second pieces of material can telescope by increasing or reducing the width of each of the first and the second attachment zones 41, 42. Hence, the same package 10 may be used to contain different sizes of flexible packages of absorbent articles 60, i.e. flexible packages comprising absorbent articles having different sizes or a different number of absorbent articles.

As for example shown in FIG. 9A, the package 10 may comprise an axis of symmetry X which is perpendicular to the first and the second side panels 21, 22. In such embodiments, the first and the second attachment zones 41, 42 are mirror images of each other.

Alternatively, the wrap-around 20 may be made of two pieces of material 51, 52 wherein the first piece of material 51 comprises the first side panel 21, a portion of the second side panel 22, the third and the fourth side panels 23, 24 and the first, second and third corner panels 31, 32, 33, 34 and the second piece of material 52 comprises a portion of the second side panel 22

The wrap-around 20 may also be made of two pieces of material 51, 52 wherein the first piece of material 51 comprises a portion of the first side panel 21, the third side panel 23, a portion of the second side panel 22 and both first and fourth corner panels 31, 34 and the second piece of material 52 comprises a portion of the first side panel 21, the fourth side panel 24, a portion of the second side panel 22 and both second and third corner panels.

Embodiments Wherein the Wrap-Around is Made of Four Pieces of Material

The wrap-around 20 may be made of four pieces of material 51, 52, 53, 54 as for example shown in FIGS. 10A and 10B.

A first piece of material 51 may comprise the first side panel 21, a portion of the third and of the fourth side panels 23, 24 and both first and second corner panels 31, 32, a second piece of material 52 may comprise the second side panel 22, a portion of the third and of the fourth side panels 23, 24 and both third and fourth corner panels 33, 34, a third piece of material 53 may comprise a portion of the third side panel 23, a fourth piece of material 54 may comprise a portion of the fourth side panel 24.

The different panels of the wrap-around 20 are made by folding each of the first and second pieces of material 51, 52 along folding lines 55 which correspond to the connecting edges 312, 321, 322, 331, 332, 341, 342, 311 of the different panels of the wrap-around 20. Such folding lines 55 are typically parallel to each other.

As for example shown in FIG. 10A, each of the first, second, third and fourth pieces of material 51, 52, 53, 54 may comprise a pair of opposing edges 511, 512, 521, 522, 531, 532, 541, 542 wherein one of the edges of the first piece of material 511, 512 is attached to one of the edges of the third piece of material 531, 532 along a first attachment zone 41 and wherein the other edge of the first piece of material 511, 512 is attached to one of the edges of the fourth piece of material 541, 542 along a second attachment zone 42. One of the edges of the second piece of material 521, 522 is attached to one of the edges of the fourth piece of material 541, 542 along a third attachment zone 43 and wherein the other edge of the second piece of material 521, 522 is attached to one of the edges of the third piece of material 531, 532 along a fourth attachment zone 44 in order to form the wrap-around 20.

The first, second, third and fourth attachment zones 41, 42, 43, 44 can have any positioning on the wrap-around 20 but embodiments wherein each of the first, second, third and fourth attachment zones 41, 42, 43, 44 are positioned in close proximity to one of the corner panels of the wrap-around 20, i.e. from 1 mm to 100 mm, or 1 mm to 50 mm away from the corner panel are particularly advantageous for the same reasons as mentioned above for the embodiments wherein the wrap-around 20 is made of a single piece of material.

As for example shown in FIG. 10A, the package 10 may comprise an axis of symmetry X which is perpendicular to the first and the second side panels 21, 22. In such embodiments, the first and the second attachment zones 41, 42 are mirror images of each other and the third and the fourth attachment zones 43, 44 are mirror images of each other.

Such embodiments wherein the wrap-around 20 is made of four pieces of material 51, 52, 53, 54 are particularly advantageous since the same package 10 may be used to contain different sizes of flexible packages of absorbent articles 60 by increasing or reducing the width of each of the first, second, third and fourth attachment zones 41, 42, 43, 44.

Alternatively, the wrap-around may be made of four pieces of material 51, 52, 53, 54, wherein the first piece of material 51 comprises a portion of the first side panel 21, a portion of the fourth side panel 24 and the second corner panel 32 and the second piece of material 52 comprises a portion of the second side panel 22, a portion of the third side panel 23 and the fourth corner panel 34 and the third piece of material 53 comprises a portion of the first side panel 21, a portion of the third side panel 23 and the first corner panel 31 and the fourth piece of material 54 comprises a portion of the second side panel 22, a portion of the fourth side panel 24 and the third corner panel 33.

In some embodiments, the wrap-around is made of three pieces of material.

The Attachment Zones

In some embodiments, as for example shown in FIGS. 8A, 9A, 10A, the attachment zones 41, 42, 43, 44 have an interior-to-exterior configuration which means that a portion of the interior surface of the wrap-around 201 is attached to a portion of the exterior surface of the wrap-around 202 in order to form the attachment zones 41, 42, 43, 44.

Figure 16:
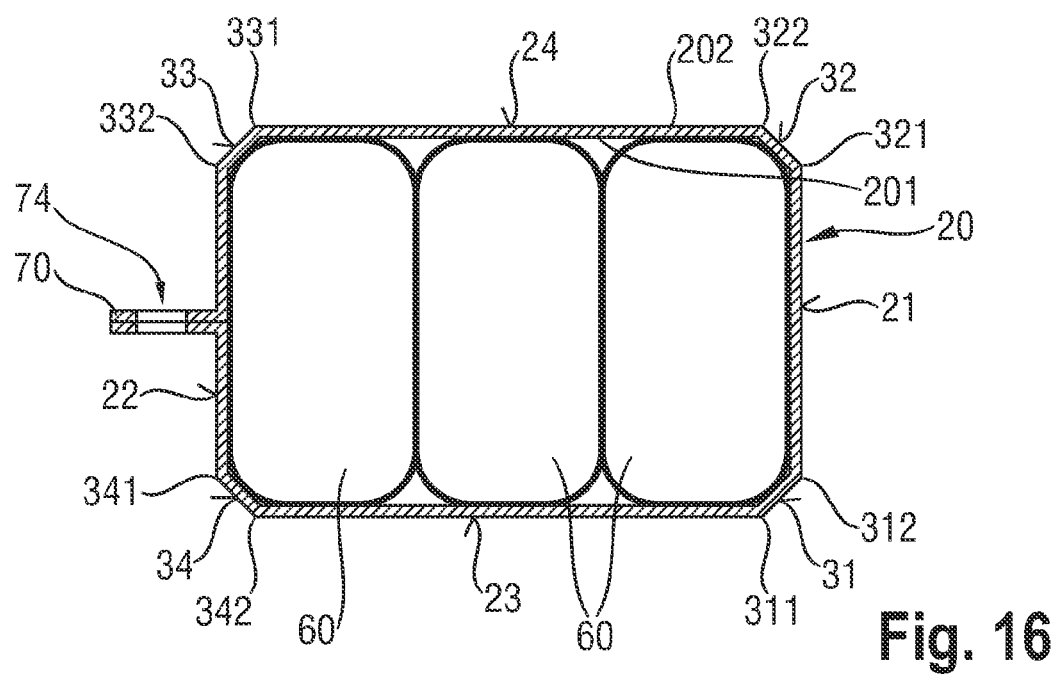
FIG. 16 is a cross-sectional view of the package of FIG. 5 taken at the section line 6-6 comprising a wrap-around made of a single piece of material having an attachment zone with an interior-to-interior configuration according to an embodiment of the present invention.

In some other embodiments, as for example shown in FIG. 16, at least one of the attachment zones 41, 42, 43, 44 has an interior-to-interior configuration which means that a portion of the interior surface of the wrap-around 201 is attached to another portion of the interior surface of the wrap-around 201 in order to form the attachment zone 41, 42, 43, 44. In such embodiments, the attachment zone 41, 42, 43, 44 is bent outwardly and a handle 70 may be made in the attachment zone 41, 42, 43, 44 by forming one or more cut-outs 74 in the attachment zone 41, 42, 43, 44. Such embodiments are particularly cost-effective since no extra material is needed in order to form the handle 70.

The attachment means that may be used in order to attach a piece of material to itself or a piece of material to another piece of material in order to form an attachment zone 41, 42, 43, 44 include adhesive bonds, heat bonds, pressure bonds, ultrasonic bonds, dynamic mechanical bonds, or any other suitable attachment means or combinations of these attachment means which are known in the art.

Shape of the Side Panels

Figure 11:
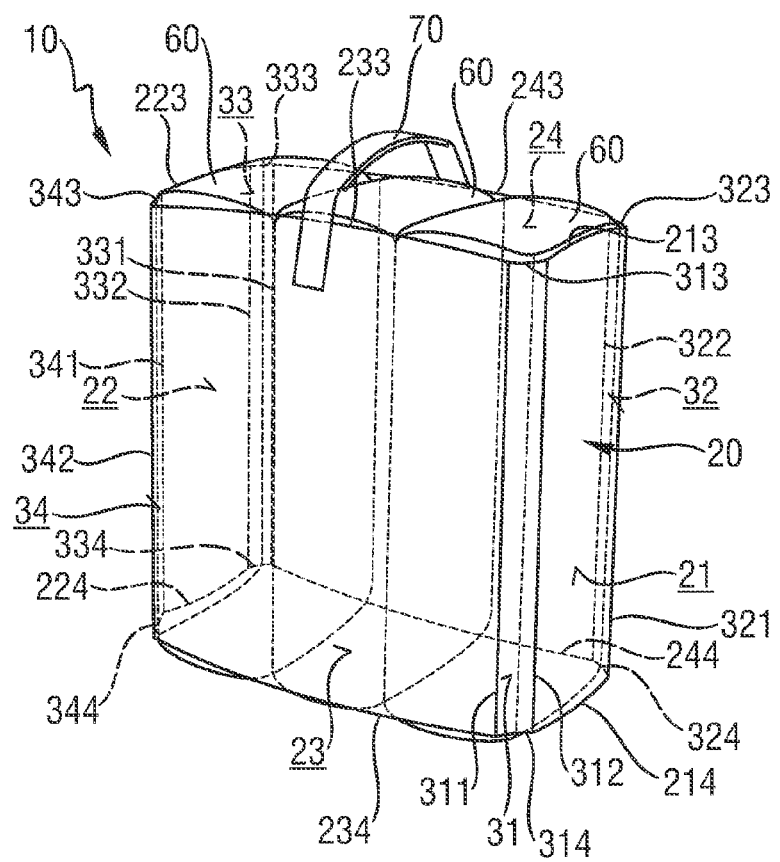
FIG. 11 is a perspective view of a package according to an embodiment of the present invention.
Figure 12:
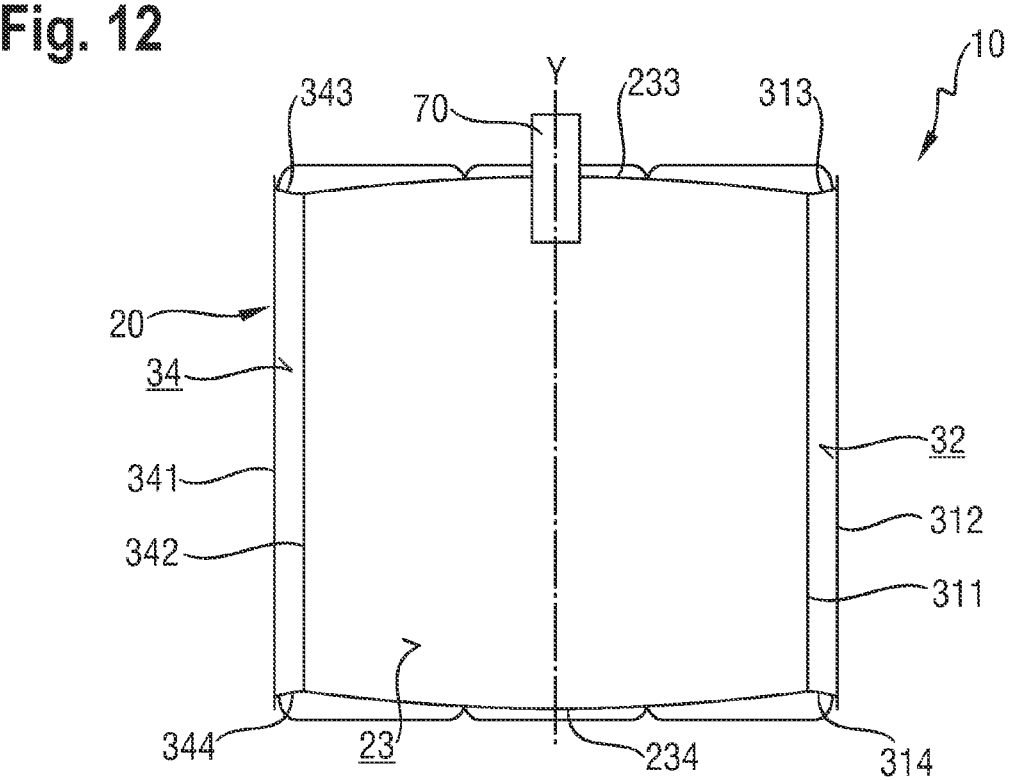
FIG. 12 is a front view of the package of FIG. 11.
Figure 13:
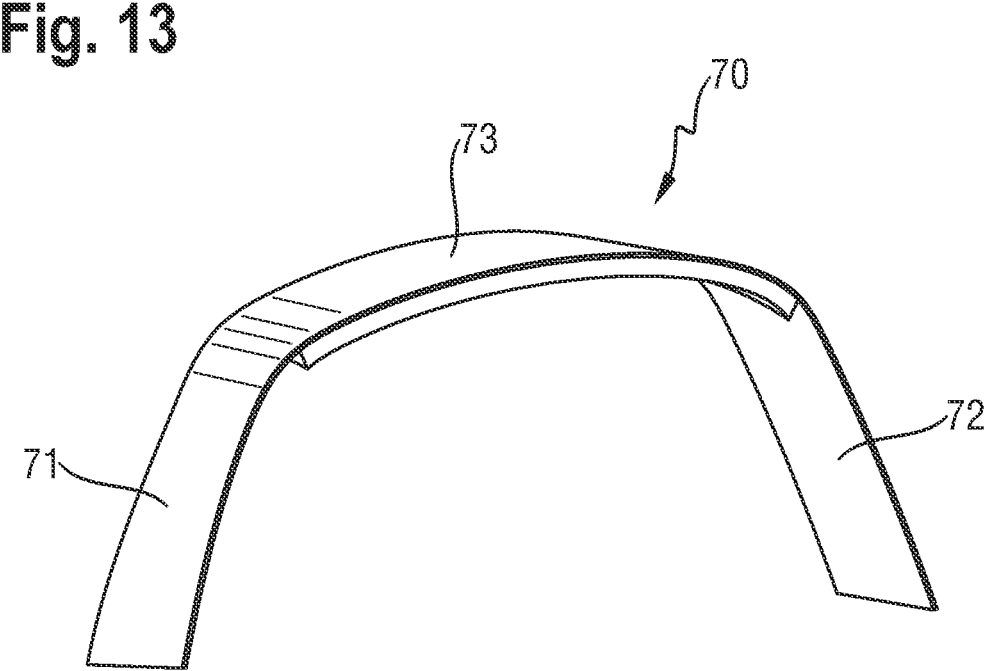
FIG. 13 is a perspective view of the handle of the package of FIG. 11.

As for example shown in FIGS. 11 and 12 at least one of the free edges 213, 214, 223, 224, 233, 234, 243, 244 of at least one of the first, second, third and fourth side panels 21, 22, 23, 24 may be convexly shaped, i.e. extend outwardly within the plane of the side panel(s). In some of these embodiments, each free edge 213, 214, 223, 224, 233, 234, 243, 244 of each of the first, second, third and fourth side panels 21, 22, 23, 24 is convexly shaped.

As for example shown in FIGS. 1 to 4, a package 10 according to the prior art is typically of parallelepiped shape and made of four side panels 21, 22, 23, 24 which are rectangular panels. When two of these packages are stacked, for example during storage, the upper package exerts a force on the lower package due to its weight. Such a force may be responsible for bending and therefore deformation of the lower package at the side portions of the side panels 80 as for example shown in FIG. 4.

Hence, it is particularly advantageous to have one or more of the free edges of the side panels 21, 22, 23, 24 which is/are convexly shaped in order to reduce the risk of bending of the package 10 at the side portions of the free edges of the side panels 80. Indeed, most of the force which is applied by the upper package to the lower package is absorbed by the middle portions of each of the free side edges which are more resistant to bending than the side portions of the free edges of the side panels 80.

These embodiments are also particularly advantageous since the risk of deformation of the package 10 is reduced without considerably reducing the size of the side panels and therefore also of the exterior surface 202 of the wrap-around 20 which typically includes printed graphics such as artworks, trademarks, logos and/or regulatory information. Since the size of the side panels is not considerably reduced, such a wrap-around 20 may maintain a good protection of the flexible packages of absorbent articles 60 which are wrapped by the wrap-around 20.

In some of these embodiments, at least one of the side panels 21, 22, 23, 24 comprises an axis of symmetry Y which is parallel to each of the connecting edges 312, 321, 322, 331, 332, 341, 342, 311 of the side panel 21, 22, 23, 24 as for example shown in FIGS. 11 and 12. In such embodiments, the length of the connecting edges of the side panel is typically shorter than the length of the side panel at the axis of symmetry Y as for example shown in FIG. 12.

Shape of the Corner Panels

The free edges 313, 314, 323, 324, 333, 334, 343, 344 of the corner panels 31, 32, 33, 34 may be straight as for example shown in FIG. 5.

At least one of the free edges 313, 314, 323, 324, 333, 334, 343, 344 of at least one of the corner panels 31, 32, 33, 34 may be concavely shaped, i.e. extend inwardly within the plane of the corner panel(s). In some of these embodiments, each free edge 313, 314, 323, 324, 333, 334, 343, 344 of each of the side panels 31, 32, 33, 34 is concavely shaped.

Flexibles Packages

In all the embodiments represented in FIGS. 5 to 14, the package 10 is shown as comprising three flexible packages of absorbent articles 60. However, this should not be considered as a limitation of the scope of these embodiments. The package 10 may comprise one or more flexible packages of absorbent articles 60, such as from 1 to 5 flexible packages, for example 1, 2, 3, 4 or 5. The flexible packages 60 may be of the same size or of different sizes. Suitable flexible packages 60 are for example described in WO2009/129202.

The interior surface 201 of the wrap-around 20 may comprise a coating or one or more adhesive tapes or a releasable adhesive in order to increase the friction force that is exerted by each of the flexible packages 60 onto the wrap-around 20. In some embodiments, only discrete areas of the interior surface 201 of the wrap-around 20 are coated in order to increase the friction force that is exerted by each of the flexible packages 60 onto the wrap-around 20. The coating may for example be in the form of a dot or a stripe pattern.

These embodiments are particularly advantageous since they provide a good immobilization of the flexible packages inside the package 10 and therefore reduce the risk that one of the flexible packages slides from the package 10.

The package 10 is wrapped either partially or completely in a plastic film or a plastic bag. The plastic film may be a shrink film or a stretch film or two sleeves of plastic film which are attached to each other.

In some embodiments, as for example shown in FIGS. 5 and 11 to 15, the package 10 comprises a handle 70. The handle 70 comprises a first and a second end portion 71, 72 and a middle portion 73.

The middle portion 73 of the handle 70 may comprise a smooth material, for example a nonwoven material.

The first and the second end portions 71, 72 are attached to the wrap-around 20.

The first end portion 71 may be attached to one of the side panels 21, 22, 23, 24 and the second end portion 72 may be attached to the opposite side panel as for example shown in FIG. 11.

Figure 14:
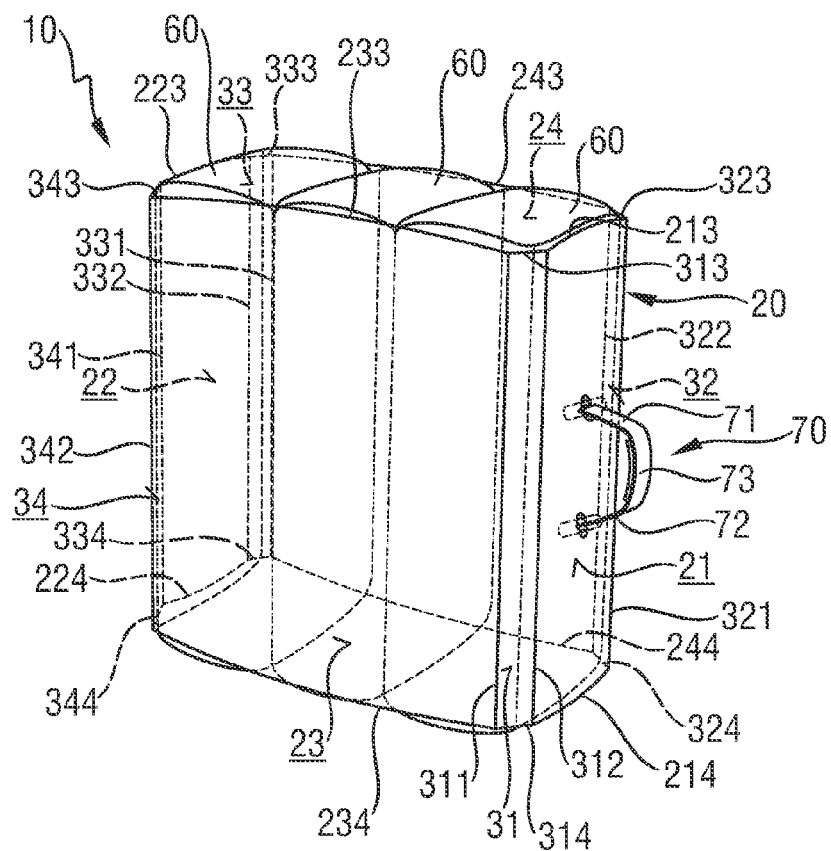
FIG. 14 is a perspective view of a package according to an embodiment of the present invention.
Figure 15:
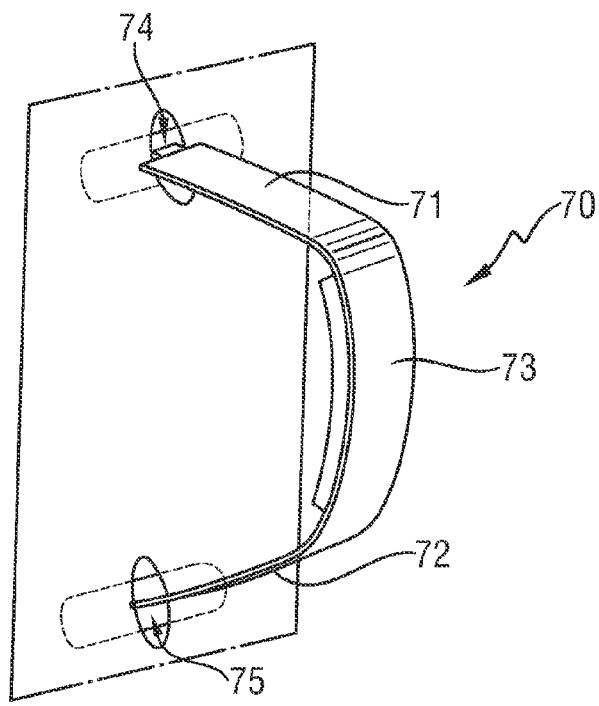
FIG. 15 is a perspective view of the handle of the package of FIG. 14.

As for example shown in FIGS. 14 and 15, the first and the second end portions 71, 72 may be attached to the same side panel 21, 22, 23, 24. The first and the second end portions 71, 72 can either be attached to the interior surface 201 or to the exterior surface 202 of the wrap-around 20. As for example shown in FIGS. 14 and 15, the side panel 21, 22, 23, 24 to which the first and the second end portions 71, 72 of the handle 70 are attached comprises one or two cut-outs 74, 75 in order to have the first and the second end portions 71, 72 of the handle 70 which are attached to the interior surface 201 of the wrap-around 20. This ensures a better anchorage of the handle 70 to the wrap-around 20.

As explained above, in some embodiments as for example shown in FIG. 16, at least one of the attachment zones 41, 42, 43, 44 has an interior-to-interior configuration. In such embodiments, the attachment zone 41, 42, 43, 44 is bent outwardly and a handle 70 may be made in the attachment zone 41, 42, 43, 44 by forming one or more cut-outs 74 in the attachment zone 41, 42, 43, 44. Such embodiments are particularly cost-effective since no extra material is needed in order to form the handle 70.

What is claimed is:

1. A package comprising one or more flexible packages contained by an outer wrap-around, the one or more flexible packages each containing a plurality of absorbent articles, wherein the wrap-around comprises:
   a first pair of opposing panels each having an opposing pair of free edges and an opposing pair of connecting edges and
   a second pair of opposing panels each having an opposing pair of free edges and an opposing pair of connecting edges,
the first pair of opposing panels being connected to the second pair of opposing panels at corners of the package, the wrap-around further comprising:
   at least a first corner panel at at least a first of the corners, wherein the first corner panel meets one of the first pair of opposing panels along a first folding line, and
   the first corner panel meets one of the second pair of opposing panels along a second folding line,
wherein the first corner panel and the respective ones of the first and second pairs of opposing panels form first and second interior angles with vertices at the first and second folding lines, respectively, and each of the first and second interior angles is from 100° to 170°.

2. The package according to claim 1, wherein the wrap-around additionally comprises:
   a second corner panel at a second of the corners, wherein the second corner panel meets one of the first pair of opposing panels along a third folding line, and the second corner panel meets one of the second pair of opposing panels along a fourth folding line;
   a third corner panel at a third of the corners, wherein the third corner panel meets one of the first pair of opposing panels along a fifth folding line, and the third corner panel meets one of the second pair of opposing panels along a sixth folding line; and
   a fourth corner panel at a fourth of the corners, wherein the fourth corner panel meets one of the first pair of opposing panels along a seventh folding line, and the fourth corner panel meets one of the second pair of opposing panels along an eighth folding line;
wherein the second, third and fourth corner panels and the respective ones of the first and second pairs of opposing panels form third, fourth, fifth, sixth, seventh and eighth interior angles with vertices at the third, fourth, fifth, sixth, seventh and eighth folding lines, respectively, and each of the third, fourth, fifth, sixth, seventh and eighth interior angles is from 100° to 170°.

3. The package according to claim 2, wherein the wrap-around is made of:
   i) a first piece of material that forms one of the first pair of opposing panels, the first and second corner panels, and first portions of each of the second pair of opposing panels; and
   ii) a second piece of material that forms the other of the first pair of opposing panels, the third and fourth corner panels, and second portions of each of the second pair of opposing panels.

4. The package according to claim 2, wherein the wrap-around is made of:
   i) a first piece of material that forms one of the first pair of opposing panels, the first and second corner panels, and first portions of each of the second pair of opposing panels;

ii) a second piece of material that forms the other of the first pair of opposing panels, the third and fourth corner panels, and second portions of each of the second pair of opposing panels;

iii) third and fourth pieces of material that form respective third and fourth portions of each of the second pair of opposing panels.

5. The package according to claim 2 wherein at least one of the corner panels is divided into two or more sub-panels each having a different orientation.

6. The package according to claim 2 wherein each of the corner panels comprises a pair of opposing free edges and a pair of connecting edges wherein at least one of the free edges is concavely shaped.

7. The package according to claim 1 wherein the wrap-around is made of a single piece of material.

8. The package according to claim 1, wherein at least one of the free edges of at least one of the opposing panels is convexly shaped.

9. The package according to claim 8 wherein the at least one of the opposing panels having the convexly shaped free edge has an axis of symmetry Y which is parallel to each of the connecting edges of at least one of the opposing panels.

10. The package according to claim 1 wherein the wrap-around comprises a material selected from the group consisting of cardboard material, corrugated board material, polymeric material and any combinations thereof.

11. The package according to claim 1 wherein an interior surface of the wrap-around comprises one of a coating, adhesive tape and adhesive that immobilizes the one or more flexible packages.

12. The package according to claim 1 wherein the package is wrapped either partially or completely in a plastic film or a plastic bag, wherein the plastic film is a shrink film or a stretch film.

13. The package according to claim 1 wherein the package further comprises a handle.

14. The package according to claim 1 wherein the absorbent articles are one of diapers, pants, sanitary napkins or any combination thereof.

* * * * *